United States Patent
Cusimano Reaston et al.

(10) Patent No.: US 8,535,224 B2
(45) Date of Patent: Sep. 17, 2013

(54) ELECTRO DIAGNOSTIC FUNCTIONAL ASSESSMENT UNIT (EFA-2)

(76) Inventors: MaryRose Cusimano Reaston, Las Vegas, NV (US); Phil Reaston, Las Vegas, NV (US)

(*) Notice: Subject to any disclaimer, the term of this patent is extended or adjusted under 35 U.S.C. 154(b) by 129 days.

(21) Appl. No.: 12/660,075

(22) Filed: Feb. 18, 2010

(65) Prior Publication Data

US 2011/0201904 A1    Aug. 18, 2011

(51) Int. Cl.
*A61B 5/00*     (2006.01)

(52) U.S. Cl.
USPC ............................ 600/301; 600/300; 128/920

(58) Field of Classification Search
None
See application file for complete search history.

(56) References Cited

U.S. PATENT DOCUMENTS

| | | | |
|---|---|---|---|
| 4,586,515 A | 5/1986 | Berger | |
| 4,667,513 A | 5/1987 | Konno | |
| 4,688,581 A | 8/1987 | Moss | |
| 4,742,832 A | 5/1988 | Kauffmann et al. | |
| 4,800,897 A | 1/1989 | Nilsson | |
| 4,805,636 A | 2/1989 | Barry et al. | |
| 4,834,057 A | 5/1989 | McLeod, Jr. | |
| 4,845,987 A | 7/1989 | Kenneth | |
| 4,886,073 A | 12/1989 | Dillon et al. | |
| 4,928,709 A | 5/1990 | Allison et al. | |
| 4,938,476 A | 7/1990 | Brunelle et al. | |
| 5,012,820 A | 5/1991 | Meyer | |
| 5,038,795 A | 8/1991 | Roush et al. | |
| 5,042,505 A | 8/1991 | Mayer et al. | |
| 5,050,618 A | 9/1991 | Larsen | |
| 5,056,530 A | 10/1991 | Butler et al. | |
| 5,462,065 A | 10/1995 | Cusimano et al. | |
| 5,513,651 A * | 5/1996 | Cusimano et al. | 600/595 |
| 6,678,549 B2 | 1/2004 | Cusimano et al. | |
| 2002/0091308 A1* | 7/2002 | Kipshidze et al. | 600/300 |
| 2002/0198473 A1* | 12/2002 | Kumar et al. | 600/595 |
| 2003/0083720 A1* | 5/2003 | Peterson et al. | 607/88 |
| 2003/0135129 A1* | 7/2003 | Cusimano et al. | 600/546 |
| 2006/0058699 A1* | 3/2006 | Vitiello et al. | 600/546 |
| 2009/0281448 A1* | 11/2009 | Wright et al. | 600/546 |
| 2009/0326406 A1* | 12/2009 | Tan et al. | 600/546 |

* cited by examiner

*Primary Examiner* — Bill Thomson
*Assistant Examiner* — Davin K Sands
(74) *Attorney, Agent, or Firm* — Albert O. Cota (57) ABSTRACT

An electro diagnostic functional assessment unit (EFA-2) that diagnoses age of and treats soft tissue injuries. The EFA-2 utilizes sensor(s) including EMG, Range of Motion, FCE, pinch and grip, and allows for monitoring of muscles and muscle groups to ascertain compliance, pain and function. The EFA-2 also monitors disc pathology and determines whether a person requires surgery or conservative care and, the age of the disc. Additionally, the EFA-2 monitors EEK activity and NCV, as well as invasive EMG that monitors nerve damage. Previously, with NCV the temperature and the position of electrodes would effect readings and produce false positive or false negative readings. The EFA-2 eliminates these problems by incorporating temperature sensor(s) and electrode placement sensor(s). The EFA-2 also provides direct treatment by means of ultrasound and electrical stimulation. Thus, the EFA-2 allows diagnosis any treatment by means of a single unit.

1 Claim, 6 Drawing Sheets

ELECTRO DIAGNOSTIC FUNCTIONAL ASSESSMENT UNIT (EFA-2)

TECHNICAL FIELD

The invention generally pertains to diagnostic treatment systems, and more particularly to a unit which specifically monitors muscle functions, cardiac functions, nerve functions, nerve conductions, temperature, heart rate, blood flow and brain activity simultaneously with range of motion including lifting, pulling, pushing, gripping and pinching. The system also allows for direct treatment by way of electrical stimulation, ultrasound or other therapeutic means.

BACKGROUND ART

A well-known medical fact is that muscle compensation patterns can be used to differentiate chronic versus acute injuries. Acute injuries are typically exemplified by muscle spasm and hyperactivity. Chronic injuries are typically associated with compensation, bilateral changes, and absence of a reflection relaxation response. It is also a proven fact that many physicians deal with complaints and injuries that derive from soft tissue injury, particularly the cervical, thoracic, lumbosacral and extremities. All muscle groups of the body, from the cervical including the scalene muscles, mid-thoracic, lumbosacral and extremities can be monitored using the applicant's Electro Diagnostic Functional Assessment Unit (EFA-2) for both humans and animals. This is extremely beneficial because most soft tissue injuries may be chronic or acute with no physical indicators. Direct palpitation of soft tissues injuries can, in some cases, reveal the nature or type of injuries but this manner of diagnosis relies on static testing. This manner of diagnosis also relies on individual tests that are performed separately, which are less reliable than combining and integrating the evaluations of Electromyography (EMG), range of motion, functional assessment, cardiac response, temperature and nerve conduction. The combinations of these tests, unlike any other test, do not rely on the coefficients of variance but measure muscle activity while simultaneously monitoring range of motion, functional assessment, grip strength, pinch strength, cardiac response, temperature and nerve conduction velocity. This dynamic integration provides an analysis of Type 1 versus Type 11 motor units, which coordinate with effort produced by the individuals. Furthermore, when disc pathology is present there is a chemical released in the blood supply which causes ischemic changes in the surrounding musculature. The benefit of quantifying the above conditions in a non-invasive and portable manner is that the amount of ischemia/vasoconstriction in the surrounding blood tissue correlates with the degree of disc pathology, thereby allowing treatment recommendations to be made, i.e., surgery versus physical therapy. The benefit of the EFA-2 is its ability to monitor and site-specifically treat various muscles or muscle groups.

In the past range of motion testing was often relied upon to determine the cause of muscle activity, however prior range of motion testing was done in two planes. The EFA-2 is able to perform testing in six planes of spinal and extremity range of motion, which captures an individual's and/or animal's complete range of motion and integrates it with electro diagnostic EMG activity. This provides pertinent information on structural as well as muscle function and relates to the nature of soft tissue injuries.

The Mayo Clinic confirmed studies on sagittal gait patterns and knee joint functions that static measurements do not correlate well with true functional assessment of movement. As part of the Mayo Clinic conclusions, they recommended the use of functional assessment as a routine diagnostic tool in a similar manner as an electro cardiogram (EKG). In this setting the use of tests such as a MRI or X-RAY are of little use since they are static tests and not specifically designed to evaluate soft tissue damage and subsequent change in function. Therefore, there is a growing need within the medical, veterinary, insurance and industrial communities for objective analysis of biomechanics on a functional level.

Myofascial injuries represent a significant medical problem, with back pain accounting for a large number of medical visits. In the United States alone 60 billion dollars a year is spent on soft tissue injuries related to worker's compensation claims and 20 billion dollars is spent on repetitive stress injuries such as Carpal Tunnel Syndrome (CTS). These injuries account for the most lost days and are currently two of the most costly health problems. The cost of these problems is expected to increase, especially with Occupational Safety and Health Administration (OSHA) considering a new ergonomic standard for repetitive stress injuries. With the implementation of the American's with Disability Act (ADA), worker's compensation claims such as CTS have increased and are expected to exceed 40 billion dollars within the next five years. These excessive claims can damage the economy and force employers to go outside of the United States. A recent study revealed that over forty-five percent of individuals who have undergone CTS relief surgery have experienced no improvement two years after the surgical intervention because they were misdiagnosed. The muscles in the anterior and posterior cervical area can cause pain and mimic symptoms of carpal tunnel syndrome, ulnar neuropathy, cubital tunnel, tendonitis, DeQuarian's syndrome and thoracic outlet syndrome. In addition, soft tissue injuries in large animals such as horses are quite prevalent and costly.

The problem is that until the development of the instant invention there was no way to ascertain if an injury was proximal, cervical or distal. Sixty-five percent of individuals who have undergone back surgery resulted in failed back syndrome or with no relief of symptomatology when the problem was myofascial or soft tissue in nature. There was no way to ascertain the extent of the myofascial pathology until the advent of the EFA-2.

The EFA-2 solves many of the above problems by enhancing, integrating and combining EMG activity to measure muscle function, range of motion testing in at least six planes for the spine and extremities, cardiac monitoring, nerve conduction studies and temperature. The EFA-2 combines up to 100 channels of proprietary surface EMG, up to 24 range of motion channels, at least 2 functional capacity evaluation sensor(s) such as those used to measure grip and pinch strength, 6 sensor(s) for cardiac monitoring, up to 4 sensor(s) for brain monitoring (EEG), a temperature sensor(s), 4 sensor(s) for nerve conduction velocity study, a blood flow sensor(s) and a heart rate sensor(s), plus electrical stimulation sensor(s) and ultrasound sensor(s) for treatment. The nerve conduction velocity (NCV) also has its own temperature sensing and preset sensor(s). In addition, the NCV can be used to deliver electrical stimulation for treatment. The EFA-2 can be battery operated and can perform remote monitoring.

A search of the prior art did not disclose literature or patents that read directly on the claims of the instant invention. However, the following U.S. patents are considered related.

| PAT. NO. | INVENTOR | ISSUED |
|---|---|---|
| 6,678,549 | Cusimano, et al | 13 Jan. 2004 |
| 5,513,657 | Cusimano, et al | 7 May 1996 |
| 5,462,065 | Cusimano, et al | 31 Oct. 1995 |
| 5,042,505 | Mayer, et al | 27 Aug. 1991 |
| 4,688,581 | Moss | 25 Aug. 1987 |
| 4,667,513 | Konno | 26 May 1987 |

The U.S. Pat. Nos. 5,513,651 and 5,462,065 patents disclose an integrated movement analyzing system that utilizes surface EMG in combination with range of motion and functional capacity testing to monitor muscle groups in the human body. The system consists of an integrated movement analyzer (IMA) that receives inputs from surface EMG sensor(s), a range of motion (ROM) and a functional capacity sensor(s). When performing upper and lower back testing, the ROM is connected between a patient's upper back and lower back by a shoulder harness and a waist belt. For cervical testing, the ROM is connected between the patient's head and upper back by a cervical cap and the shoulder harness. The output of the IMA is provided via an analog to digital converter to a computer. The computer, in combination with a software program, produces an output consisting of comparative analytical data. This data is taken via a parallel port and multiple a/d cards while the patient is not isolated. The unit is not integrated and cumbersome.

The U.S. Pat. No. 5,042,505 patent discloses an electronic device for measuring relative angular positional displacement and angular range of motion for body segments and articulating joints of the human skeleton. The device has a hand-held interface unit, which is placed against the body segment or joint to be tested. Mounted within the housing of the interface unit is a shaft with a pendulum at one end and an optical encoder at the other. As the body segment rotates or the joint articulates, the pendulum swings in the direction of gravity, causing the shaft to rotate. The optical encoder generates an electrical signal representative of the amount of rotation of the shaft. The generated signal is fed to a microscope which processes the information and can produce or display the change in angular position relative to initial angular position or the angular range of motion of the body segment or articulating joint.

The U.S. Pat. No. 4,688,581 patent discloses an apparatus and a method for non-invasive in-vivo determination of muscle fiber composition. The method includes the steps of electrically stimulating a chosen muscle, determining the stimulation current; measuring the electrical potential of the muscle, the contraction time and the force produced by the contraction and by intercorrelating the data by multiple regression, thereby determining the type, percentage and size of the muscle fibers within the muscle stimulated. The apparatus for determining the muscle composition includes a muscle stimulator of controlled voltage electromygram equipment and a force transducer, thus providing a tension curve as well as force measurements.

The U.S. Pat. No. 4,667,513 patent discloses an apparatus and a method for estimating the degree of fatigue and pain of muscles. The apparatus composes subjects of different weights on the same basis by deriving variations in the muscular strength such as dorsal muscular strength, shoulder muscular strength, grasping power and the like. An analogous electric signal integrates the muscular output on one hand, and provides an integrated value of the electromyogrammatic amplitude by processing the voltage induced from the muscle to be tested through an electromygram amplitude and waveform processor. The ratio between these integrated values after correlating the ratio with the weight/muscular strength coefficient is digitally displayed.

The U.S. Pat. No. 6,678,549 patent discloses a system that combines EMG, ROM and NCV. The system does not allow remote monitoring, blood flow monitoring or different ROM. The system uses an interface that does not allow for the rapid exchange of data, uses multiple data acquisition cards that do not have data consistency and is not an integrated unit, thereby making it cumbersome and less reliable. It is also only for humans, not animals.

For background purposes and as indicative of the art to which the invention relates, reference may be made to the following remaining patents found in the search.

| PAT. NO. | INVENTOR | ISSUED |
|---|---|---|
| 5,056,530 | Butler, et al | 15 Oct. 1991 |
| 5,050,618 | Larsen | 24 Sep. 1991 |
| 5,042,505 | Meyer, et al | 27 Aug. 1991 |
| 5,038,795 | Roush, et al | 13 Aug. 1991 |
| 5,012,820 | Meyer | 7 May 1991 |
| 4,938,476 | Bryunnell, et al | 3 Jul. 1990 |
| 4,928,709 | Allison, et al | 29 Jul. 1990 |
| 4,886,073 | Dillion, et al | 12 Dec. 1989 |
| 4,845,987 | Kenneth | 11 Jul. 1989 |
| 4,834,057 | McLeod, Jr. | 30 May 1989 |
| 4,805,636 | Barry, et al | 21 Feb. 1989 |
| 4,800,897 | Nilsson | 31 Jan. 1989 |
| 4,742,832 | Kauffmann, et al | 10 May 1988 |
| 4,667,513 | Konno | 26 May 1987 |
| 4,586,515 | Berger | 6 May 1986 |

The EFA-2 performs all the physiological monitoring, i.e., muscles nerves, brain waves, cardiac, blood flow, heart rate, range of motion and functional capacities into one invention. In addition, the EFA-2 offers therapeutic capabilities. None of the other systems offer therapeutic intervention and complete physiological monitoring. Also, the EFA-2 offers remote monitoring.

DISCLOSURE OF THE INVENTION

The Electro Diagnostic Functional Assessment Unit (EFA-2) consists of a portable, integrated, self-contained, non-loading electronic unit that simultaneously monitors muscle activity with standard off-the-shelf silver chloride sensor(s). The muscle groups in the human/animal body that are monitored include: cervical, cranial, thoracic lumbosacral, upper extremities and lower extremities. Standard sensor(s) are used to monitor cardiac function. The EFA-2 also combines a load cell and two strain gauges to determine a patient's lifting, pushing, pulling, gripping and pinching capabilities with range of motion ability. The EFA-2 functions in tandem with an integrated computer that includes a touch screen and/or attached keyboard and pointing device. The EFA-2 utilizes a proprietary software program titled EFA-2 Data Acquisition System which correlates muscle activity with range of motion, cardiac activity, temperature, lifting, pushing, pulling, gripping and pinching. The design of the EFA-2 allows for electromyography (EMG), range-of-motion (ROM) (spinal, upper extremities, lower extremities and hip and digits), grip assessment, pinch assessment, functional capacity evaluation (FCE), cardiac assessment, temperature assessment and nerve conduction studies to be conducted during a single testing session. The EFA-2 also allows monitoring of cardiac, blood flow, heart rate, nerve conduction velocity (NCV), EEG and remote monitoring. The unit also allows for integration of site specific treatment modalities such as ultrasound or electrical stimulation.

In addition, the advantage of the EFA-2 is that it combines all physiological monitoring for diagnostic purposes with site-specific treatment modalities. This is accomplished by integrating the electrical stimulation and ultrasound capabilities of the EFA-2.

During an injury to a muscle and/or fascial element, many pathophysiological processes occur which follow a predictable pattern. When a muscle is strained, the fibers of the muscle are damaged and cells within the muscle are ruptured. The ruptured cells release substances which cause the muscle to reflexively tighten. Muscles that cause an action (agonist) and muscles which prevent the action (antagonist) are monitored. Muscle groups which are distant from the injury site may not be performing up to their proper functions, they are compensating for the loss of function due to the injury. The greater the pattern of compensation the more longstanding the injury. The absence of a flexion relaxation response of the cervical, thoracic and lumbosacral spines are also consistent with a chronic injury. The EFA-2 monitors muscle activity amplitude changes that correlate with contracture and frequency changes which correlate to spasms. Ischemic changes are monitored and bilateral assessments are made for comparison. Muscle groups above and below the injury site are monitored to determine primary, secondary and tertiary patterns.

The contraction and amplitude of the EMG response also correlate with a chronic versus acute injury. The process of aging an injury is multi-factorial and involves not only muscle groups but their inter-relationship with each other. The process also requires range of motion testing which is conducted with either the use of potentiometers or accelerometers onto appropriate body positions to correlate with spinal conditions such as straightening of the cervical spine, spondolyothesis, degenerative disk disease and post-surgical changes. The range of motion combined with the EMG monitoring is also a factor in the aging of the injury. The EFA-2 can monitor up to 100 EMG channels, up to 24 range of motion channels, up to 6 cardiac channels, 1 temperature channel, up to 4 EEG channels, 1 heart channel, 1 blood flow channel and 4 channels for nerve conduction velocity simultaneously. In addition to the diagnostic capabilities, the EFA-2 offers therapeutic capabilities of electrical stimulation and ultrasound to be site-specifically delivered after or concurrent with the site-specific diagnosis being monitored. Also, the EFA-2 has remote monitoring capabilities, i.e., the testing can be conducted from a remote physical location via the computer access.

By understanding the natural progression of a myofascial injury, and the information provided by the EFA-2, the relative age of an injury can be determined. In its most basic form, the EFA-2 is comprised of the following elements:
a) EMG sensor(s),
b) Range-of-motion sensor(s),
c) Functional capacity evaluation sensor(s),
d) Grip strength sensor(s),
e) Pinch sensor(s),
f) On-board processor,
g) Computer,
h) EKG sensor(s),
i) NCV sensors(s),
j) Temperature sensor(s),
k) Heart rate sensor(s),
l) Blood flow sensor(s),
m) Electrical stimulation delivery sensor(s),
n) Ultrasound delivery sensor(s),
o) EEG sensor(s),
p) Software,
q) EFA-2 control circuit and
r) level sensor(s).

In view of the above disclosure, the primary object of the EFA-2 is to monitor human or animal muscle activity which includes any muscle group in the body, fascial, cervical, thoracic, upper and lower extremities, lumbosacral, and similarly in large animals including torso, legs, neck and face. The EFA-2 can simultaneously correlate the muscle activity, (EMG) with cardiac activity, nerve activity, heart rate blood flow and brain activity with range-of-motion, grip assessment and range-of-motion in humans, animals, grip assessment and a functional capacity evaluation in human and grip and pinch assessments in humans. An EMG sensor has means for producing and delivering a current specifically to provide site-specific treatment or to sense the amplitude and frequency and conduction velocity of specific nerves of a person's or animals' muscle groups or nerve fibers. Furthermore, temperature and nerve conduction velocity (NCV) can be monitored in humans and animals. In addition, the EFA-2 can provide therapeutic intervention via electrical stimulation and ultrasound, and remote monitoring. The EFA-2 identified compliant individuals, malingering individuals, and individuals who have pain. Most importantly, the FA-2 is used to diagnose real injuries and allow the acquired data to be reviewed in order to determine appropriate medical treatment.

In addition to the primary object of the invention, it is also an object of the invention to provide an EFA-2 that:
Assesses the extent of myofascial injures and to determine if the injuries relate to any mechanics of an injury or pathology,
Assesses the extent of nerve injures to determine if the injuries to any injury or pathology,
Accesses the heart rate to determine if it relates to compliance, injury or pathology,
Accesses the brain activity to determine if it relates to an injury or pathology,
Allows muscle pathology to be assessed above and below the area of the reported injury, which allows for the extent of an injury to be established, to determine future treatment, allows for cardiac temperature and nerve conduction velocity to be measured to ascertain not only myofascial nerve and structural injuries but also the possibility of permanent disability, surgical intervention, treatment and vocational rehab in both humans and animals,
Provides the real time diagnosis of muscle activity, EKG activity, structural activity, nerve activity and temperature,
Provides a powerful tool for establishing an evaluation and treatment program and especially site-specific treatment,
Provides remote monitoring which allows experts who are not at the physical location to evaluate an individual,
Assesses chronic versus acute injuries by evaluating muscle composition, and evaluate EKG activity as a preventative measure to prevent cardiac problems,
Assesses nerve conduction velocity and bilateral comparison with preset temperature sensor(s) for injury as well as prevention assessments,
Assists physicians who care for athletes and determine the extend of sports related muscular skeletal injuries and provide accurate data that can be used in designing site-specific treatment protocols, therefore allowing a more rapid, predictable and safe return to competition. The EFA-2 can be used as a pre-physical examination to allow trainers of both humans and animals to address otherwise undiagnosed deficiencies in the muscular, skeletal, cardiac, nerve, blood flow and temperature, and Assesses the clinical significance of disc pathology, In summary, the EFA-2 identifies the severity of injuries and allows for the establishment of future diagnostic and treatment programs that take into account both the needs of the treated person or animal, the need to contain runaway costs of potential long-term or unsubstantiated cases, and allows for site-specific treatment to be delivered, thereby aiding the patient and reducing costs.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms that disclose a preferred embodiment of an Electro Diagnostic Functional Assessment Unit (EFA-2). The EFA-2 performs an electro diagnostic functional assessment test by analyzing muscle activity by means of electromyography (EMG). When using EMG/NCV/EEG/ECG, a standard silver-silver chloride sensor(s) is attached to a muscle or muscle group. The electrical activity of the muscle or muscle group is then measured and recorded. Furthermore, a specific EMG activity and filtering system is used to monitor cardiac muscle, EKG activity. The EFA-2 is configured to perform site-specific treatment based on the combination of measured functions derived from multiple sensors.

The muscle groups monitored by the EFA-2 are: facial, cervical, thoracic, lumbosacral and upper extremity and lower extremity in both humans and animals. Data pertaining to each muscle group is typically taken in the following five steps, while the monitored muscle or muscle group is:

1) At rest,
2) Going through a range of motion protocol,
3) At rest,
4) Being applied a functional assessment which for humans consists of gripping, pinching, lifting, pulling and pushing, and
5) At rest.

The following can be performed or collected depending on the requirements of a particular test:

1) EKG activity,
2) Temperature,
3) EEG activity,
4) Heart rate,
5) Blood flow,
6) Site-specific therapy that is delivered via the ultrasound and electrical stimulation capabilities,
7) Remote monitoring can be conducted, and
8) Nerve conduction velocity.

The above modalities allow the EFA-2 to determine muscle tone (contracture amplitude), muscle spasms (frequency), blood flow to muscle (vasoconstrictive states), muscle activity (frequency and recruitment patterns), muscle response (fatigue), cardiac response (EKG), nerve conduction velocity, heart rate, blood flow, brain activity (EEG) and temperature in both humans and animals. Thus the EFA-2 can assess the condition and the dynamic functions of any particular muscle or muscle group in the body for animals and humans. The EFA-2 then allows for the delivery of site-specific treatment and/or remote monitoring.

In a typical configuration the EFA-2 is comprised of a) Up to 100 channels of EMG wherein each channel can be designed to incorporate an analog-to-digital converter (ADC),
b) Up to six channels of EKG,
c) Up to four channels of nerve conductive velocity (NCV) with temperature control and preset sensor(s),
d) Up to 24 channels of range of motion (ROM),
e) Two channels for functional capacity evaluation (FCE),
f) A channel for grip strength,
g) A channel for pinch strength,
h) A channel for temperature,
i) A channel for delivering ultrasound,
j) A channel for delivering electrical stimulation, and
k) Sensor(s) for detecting lead-fail conditions.

The preferred embodiment of the EFA-2, as shown in FIGS. 1-5, is comprised of the following major elements: at least one EMG sensor 4, at least one EKG sensor 6, at least one animal range of motion (ROM) sensor 8, at least one human ROM sensor 10, at least one temperature sensor 12, at least one function at least one functional capacity evaluation (FCE) sensor 14, at least one Galvanic Skin Response (GSR) sensor 16, at least one grip strength sensor 18, at least one pinch strength sensor 20, at least one Nerve Conduction Velocity (NCV) sensor 22, at least one level sensor 24, an ultrasound/delivery mechanism 26, at least one heart rate sensor 28, an electrical stimulation/delivery mechanism, 30, at least one EEG sensor 32, at least one blood flow sensor 34, an EFA-2 control circuit 36, a computer/software circuit 40 comprising a patient software program 40, a computer 42, a computer system interface circuit 44, a power supply circuit 46, a power supply interface circuit 48, a digital supply 50, an analog power supply 52, and a cable assembly 106. Additionally, there is at least one treatment delivery mechanism having means for delivering site-specific treatment, wherein the output from said at least one treatment delivery mechanism is applied to and processed by said EFA-2 is configured which is configured to perform site-specific treatment.

Figure 1A:
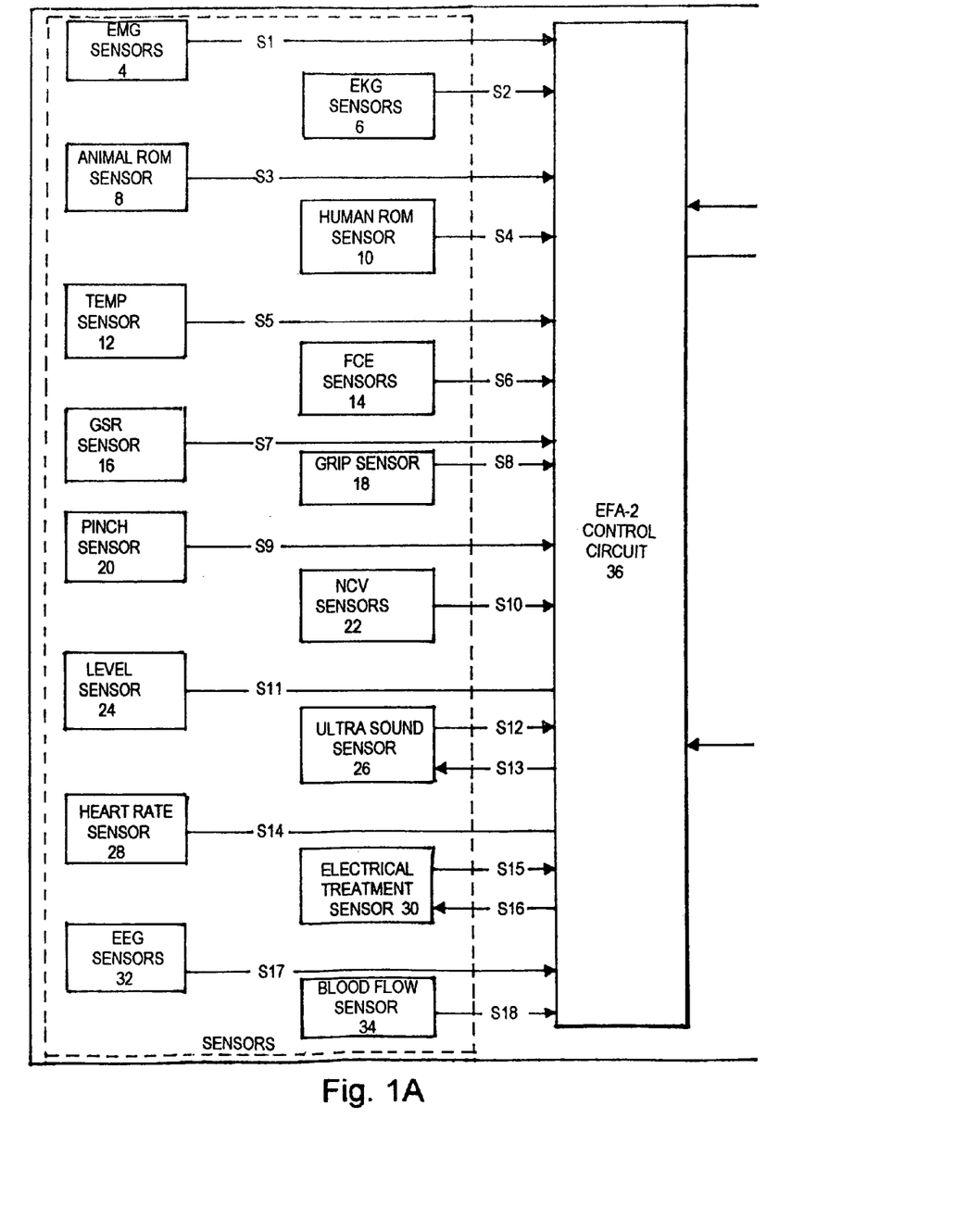
FIGS. 1A and 1B are block diagrams of the overall EFA-2.
Figure 1B:
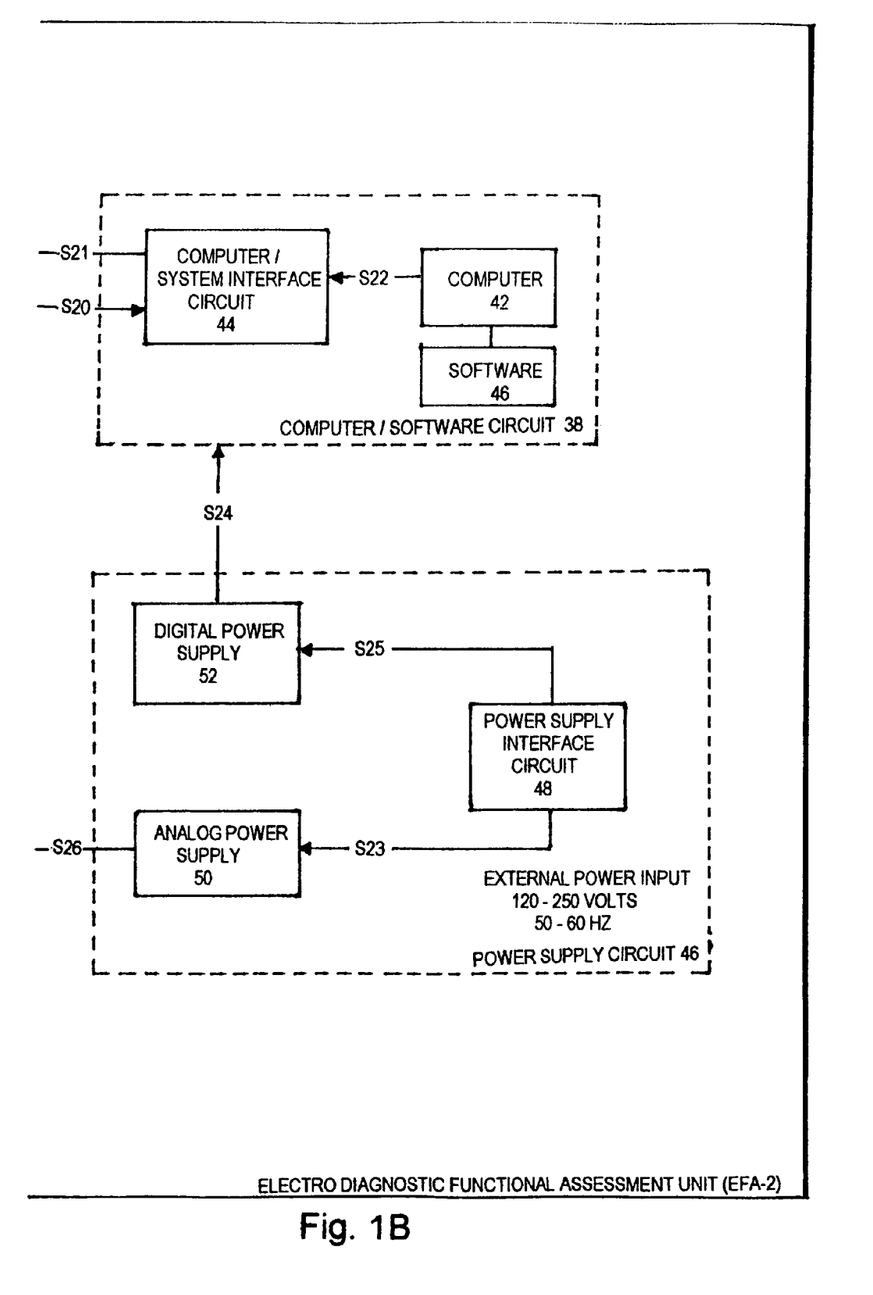
Figure 2A:
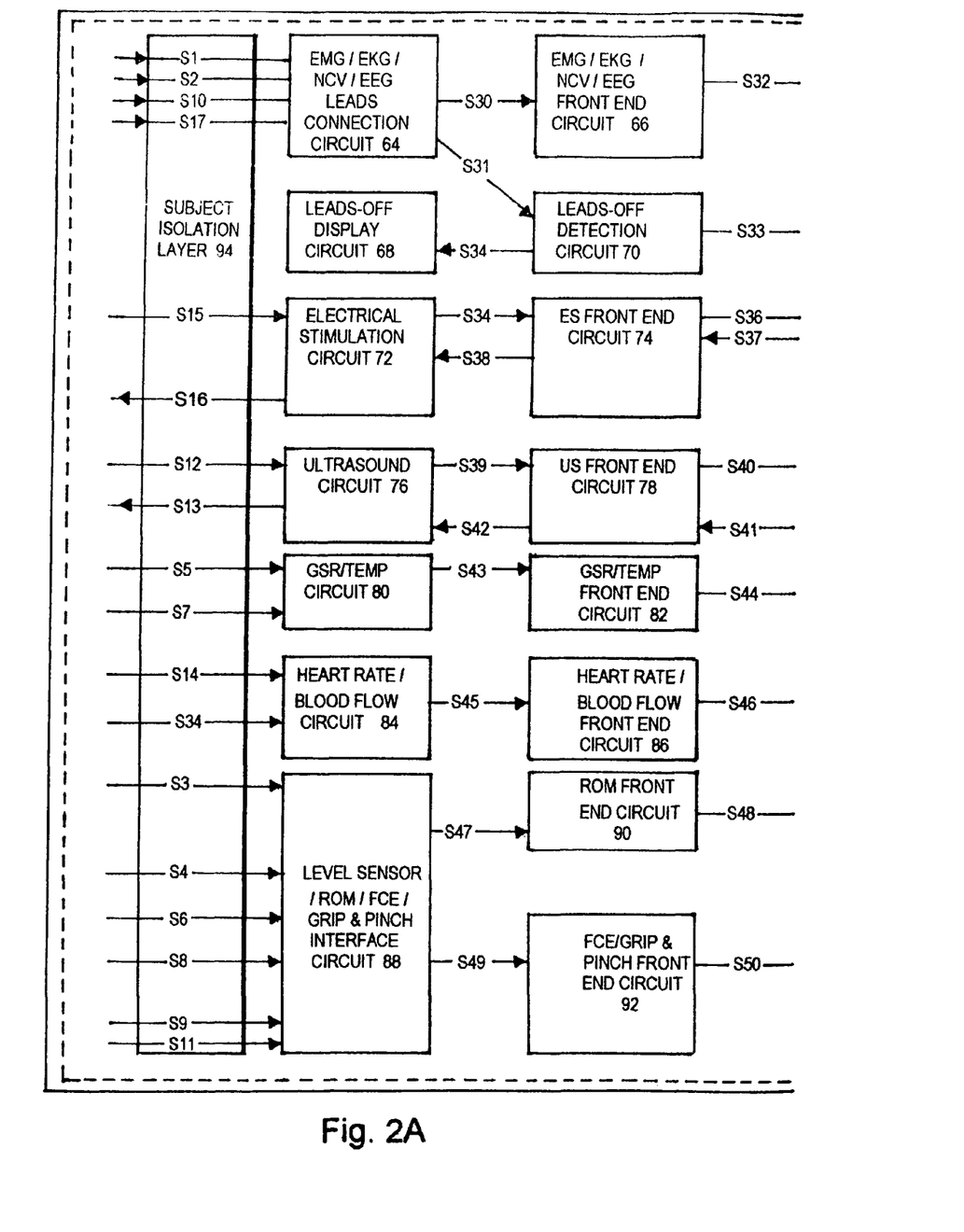
FIGS. 2A and 2B are block diagrams of the overall EFA-2 control circuit, which is integral element of the EFA-2.
Figure 2B:
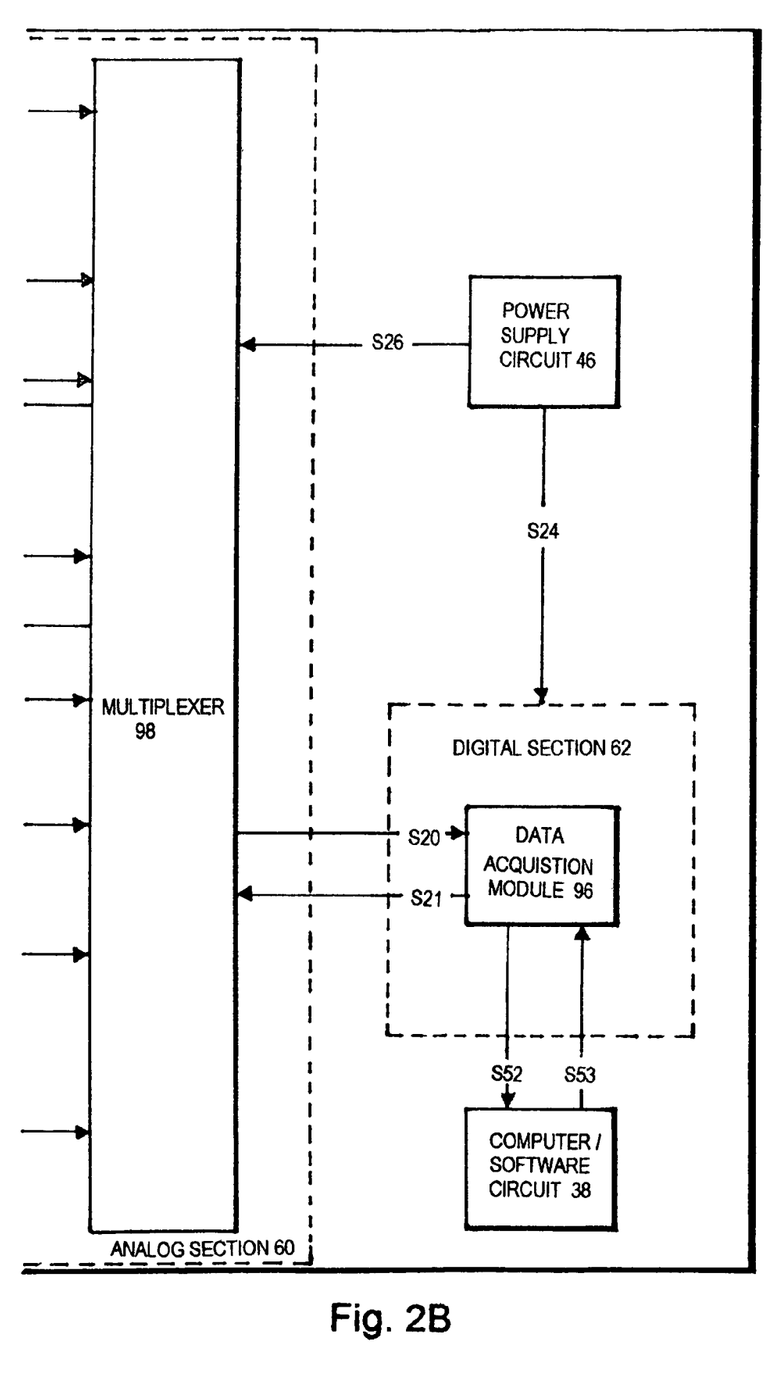

The EFA-2 control circuit 36 has means for processing the digital and analog signals which operate the EFA-2 2. The EFA-2 control circuit 36, which is shown in its overall relationship with the EFA-2 2 in FIGS. 1A and 1B, and in detail in FIGS. 2A and 2B, is partitioned into an analog section 60, a digital section 62 and a power distribution circuit 46 using medical grade power supplies. The analog section 60 is comprised of EMG/EKG/NCV/EEG leads connection circuitry 64, an EMG/EKG/NCV/EEG front end circuit 66, a leads-off detection circuit 70, a leads-off display circuit 68, an Electrical Stimulation (ES) circuit 72, an ES front end circuit 74, an Ultrasound circuit 76, an ultrasound front end circuit 78, a GSR/temperature circuit 80, a GSR/temperature front end circuit 82, a heart rate/blood flow circuit 84, a heart rate/blood flow front end circuit 86, a level sensor(s)/range-of-motion/functional capacity evaluation/grip and pinch interface circuit 88, a range-of-motion front end circuit 90, an FCE/grip and pinch front end circuit 92, a subject isolation layer 94, a multiplexer 98 and a data acquisition module 96.

The EMG/EKG/NCV/EEG section of the EFA-2 control circuit 36 begins with signals s1, s2, s10, and s17 being passed through the subject isolation layer 94 in order to isolate the subject from any potentially dangerous voltages. The resulting signals are fed into the EMG/EKG/NCV/EEG leads connection circuit 64 which has means for determining the structural integrity of the leads from the EMG/EKG/NCV/EEG sensor(s) and can accommodate from one to 100 leads. The circuit 64 is connected to the EMG/EKG/NCV/EEG front end circuit 66 via signal s30 and to the leads-off detection circuit 70 via signal s31.

The EMG/EKG/NCV/EEG front end circuit 66 has means for assessing the muscle activity, nerve activity, cardiac activity, and brain wave activity by the EMG/EKG/NCV/EEG sensor(s) based on the amplified and filtered resistance between a pair of EMG sensor(s). The EMG/EKG/NCV/EEG front end circuit 66 produces a signal s32 applied to the multiplexer 98 and thence via signal s20 to the data acquisition circuit for further processing. The leads-off detection circuit 70 has means for determining if the EMG/EKG/NCV/EEG sensor(s) leads are properly attached by measuring the impedance of the muscle and the surrounding skin area. The leads-off detection circuit 70 is connected via signal s33 to the data acquisition module 96 for further processing and to the leads-off display circuit 68 which has means for producing a display when an sensor(s) attached to a muscle or the surrounding skin is not properly attached or there is excessive activity coming from that site. This determination is made by measuring the impedance of each sensor(s). If the impedance is not at a correct level, a corresponding LED changes from green to white. The circuit 70 allows for up to 112 sensor(s) to be utilized, wherein each sensor(s) pertains to EMG, EKG, EEG or nerve placement. The leads-off detection circuit 70 also has means to pass signal s33 to the multiplexer and then via signal s20 to the data acquisition module 96 for further processing.

The electrical stimulation circuit 72 receives an input from the electrical stimulation sensor(s) 30 via signal s15. The signal s15 is passed through the subject isolation layer 94 before being applied to the electrical stimulation front-end circuit 74 via signal s34 for amplification and filtering prior to being sent to the data acquisition module 96 for processing via signals s36 and s20. The electrical stimulation front-end circuit 74 also receives input back from the data acquisition module via signals s21 and s37. Signal s37 is processed to determine the appropriate electrical stimulation and signal s38 is passed to the electrical stimulation circuit 72. The circuit 72 electrical stimulation is sent back to the electrical stimulation sensor(s) 30 via signal s16.

The ultrasound circuit 76 receives an input from the ultrasound sensor(s) 26 via signal s12. The signal s12 is passed through the subject's isolation layer 94 before being applied to the ultrasound front-end circuit 78 via signal s39 for amplification and filtering prior to being sent to the data acquisition module 96 for processing via signals s40 and s20. The ultrasound front-end circuit 78 also receives input back from the data acquisition module via signals s21 and s41. Signal s41 is processed to deliver the ultrasound and signal s42 is passed to the ultrasound circuit 76. From circuit 76 the ultrasound is sent back to the ultrasound sensor(s) 26 via signal s13.

The GSR temperature circuit 80 receives an input from the GSR sensor(s) 16 via signal s7 and the temperature sensor(s) 12 via signal s5. The resulting signal s43 is sent to the GSR/temperature front-end circuit 82 for amplification and filtering and then via signals s44 and s20 to the data acquisition module 96 for further processing.

The heart rate/blood flow circuit 84 receives an input from the heart rate sensor(s) 23 via signal s14 and the blood flow sensor(s) 34 via signal s18. The resulting signal s45 is sent to the heart rate/blood flow front-end circuit 86 for amplification and filtering and then via signals s46 and s20 to the data acquisition module 96 for further processing.

The level sensor(s)/range-of-motion (ROM) functional capacity evaluation FCE/grip and pinch interface circuit 88 is shown in FIG. 2 as a single element.

The circuit 88 inputs signals s3, s4, s6, s8, s9 and s11 which are connected respectively to animal ROM sensor(s) 8, human ROM sensor(s) 10, FCE sensor(s) 14, a grip sensor(s) 18, a pinch sensor(s) 20 and a level sensor(s) 24. The circuit 88 produces a signal s47 which is applied to the ROM front end circuit 90 and a signal s49 which is applied to the FCE/grip and pinch front end circuit 92.

The ROM front end circuit 90 has means for receiving and processing the data applied from the circuit via signal s47. The received data is amplified and filtered prior to producing signals s48 and s21 that is applied to the data acquisition module for further processing.

The FCE/grip and pinch front-end circuit 92 has means for receiving and processing the data applied from the circuit via signal s49. The received data is amplified and filtered prior to producing signals s50 and s21 that is applied to the data acquisition module for further processing.

The digital section 62 of the EFA-2 control circuit is comprised of a Data Acquisition module 96 which is capable of inputting both analog and digital signals. Digital signals are passed directly to the computer/software circuit 38 for processing via signal s52. Analog signals are first converted to digital prior to being passed to the computer/software circuit 38 for processing via signal s52. The computer/software circuit 38 is also capable of passing signals back through the data acquisition module 96 via signal s52. The data acquisition module 96 then passes these back to the analog section 60 via signal s21. The data acquisition module 96 is connected to the computer/software circuit by whatever computer interface techniques are appropriate (e.g., PCI, PCMIA, USB, Firewire, wireless etc.). The circuit 38 is designed to interface with the software via the computer.

The final element of the EFA-2 control circuit is the power supply circuit 46, which regulates and distributes digital power via signals s25 and s24 and an analog power via signals s23 and s26.

The ROM includes means for measuring the range of motion in the cervical, thoracic, lumbosacral, upper extremities, lower extremities and digits. The ROM measures a person's lateral movement, flexion, extension, rotation, abduction, adduction, lateral movements and internal and external rotation with each movement having a minimum of six degrees of freedom. The ROM incorporates three triaxial silicon micro-matched accelerator/potentiometer systems, with each system including three precision potentiometers or hermetically sealed accelerometers. The ROM has a bandwidth of 7 hertz to 4 kilohertz and, if required, can be a-c coupled. Optimally, the ROM is designed for monitoring spinal/joint changes.

The functional capacity evaluation (FCR) sensor(s) include means for measuring a person's lifting, pulling and pushing capability. The FCE sensor(s) function by utilizing load cells with a range of 0 to 300 pounds which produce analog signals. The grip/pinch sensor(s) include means for measuring a person's handgrip strength and pinch strength. The handgrip strength is measured by a load cell which produces an analog signal that is proportional to the grip force. The pinch strength is measured by a load cell which has a range of 0 to 50 pounds and is placed between the thumb and index finger and squeezed to produce an analog signal. The temperature sensor(s) include means for measuring a person's temperature in centigrade and Fahrenheit. The NCV sensor(s) include means for measuring nerve condition velocity in any muscle group in the body with present sensor(s) that control the temperature. This produces an analog signal that is proportional to the conduction. The EKG includes means for measuring a person's cardiac response which is measured in the 7 to 10 hertz range. The EKG channel also located in the EFA-2 control circuit. The EEG sensor(s) include means for measuring brain activity.

The power input to the EFA-2 is provided by an external power source that is applied to a power supply interface which has means for receiving and processing a power input ranging from 120 to 250 volts a-c at a frequency of 50 or 60 hertz. The power supply interface circuit incorporates circuit protection in the form of a circuit breaker or fuse. The analog power supply produces a regulated 5 volts d-c which powers the analog circuits in the EFA-2 control circuit. Likewise, the digital power supply, which is isolated from the analog power supply, produces a regulated 5 volt d-c which powers the EFA-2. The EFA-2 can also be battery operated.

Figure 3:
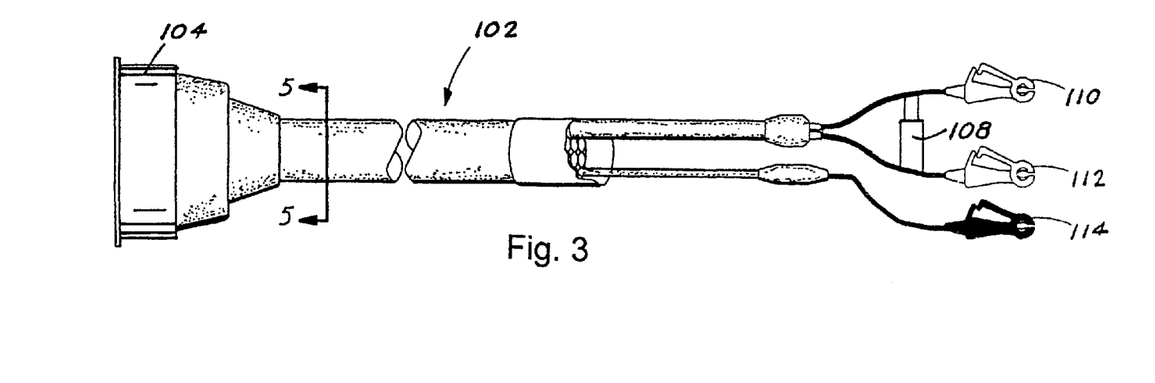
FIG. 3 is a side elevational view of an electromyograph (EMG) cable assembly.
Figure 4:
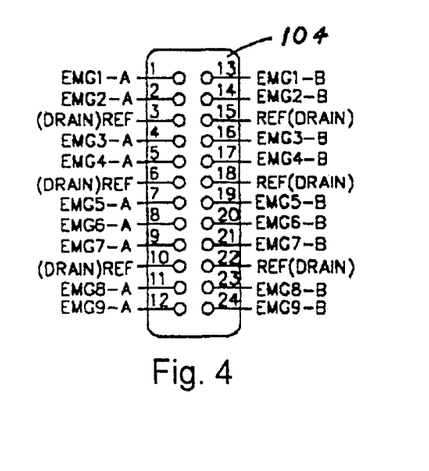
FIG. 4 is a side elevational view of the multi-pin connector of the EMG cable assembly.
Figure 5:
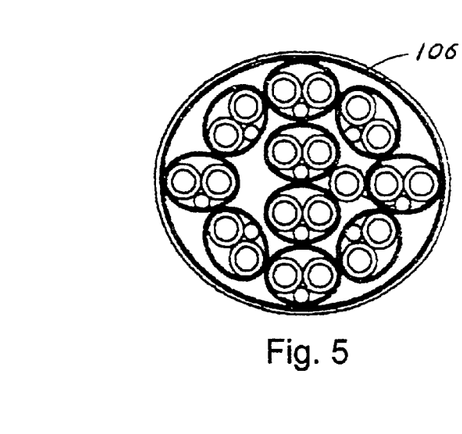
FIG. 5 is a sectional view of the EMG cable assembly taken along the lines of 5-5 of FIG. 3.
Figure 6:
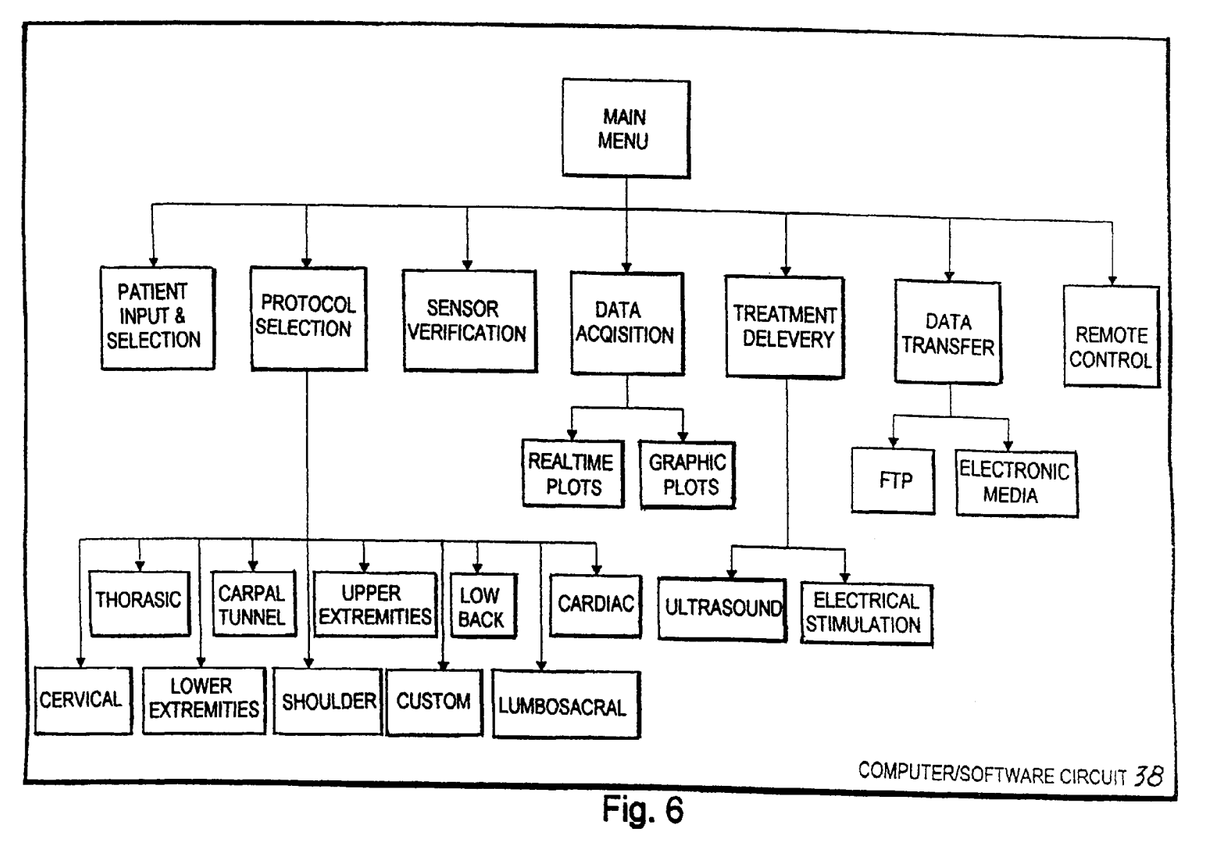
FIG. 6 is a module flow diagram of the EFA-2 software program.

An EMG/EKG/NCV/EEG cable assembly 106, as shown in FIGS. 4, 5 and 6, is designed to connect the EMG/EKG/NCV/EEG sensor(s) to the muscle or muscle group, nerves or brain of a person or animal being tested. The cable includes a multi-pin connector 104, as shown in FIGS. 3 and 4; ten shielded wire pairs, as shown in FIG. 5; and two EMG sensor(s) 110,112 with one universal ground 114, as shown in FIG. 3. The first is active which is common with the second which is also active. The third is the general reference circuit ground.

The EMG cable assembly 102 when performing NCV incorporates a separation bar 108, as shown in FIG. 4, which can be locked at a distance between 3 to 5 inches. The separation bar 108 allows the two active sensor(s) 110,112 to remain isolated from each other. Additionally, the EMG cable assembly 102 can be designed to include a temperature sensor(s) that allows temperature readings to be taken in combination with other EMG/NCV sensor(s) readings.

The software 38 is designed to control the collection of data for the EFA-2 and to control delivery of site-specific treatment which is based on information derived from the combined use of the sensors. The software has capabilities for remote monitoring such that the test can be overseen and controlled from a remote location through a connection such as the Internet. The software provides error detection and interactive computer interfaces, and resides in a dedicated computer, which can be integrated into the EFA-2 design or can be stand alone. For safety reasons a medical grade computer should be used. The computer is connected via signals s52 and s53 to the data acquisition module 96 which allows the computer to communicate with the EFA-2 via the EFA-2 control circuit, as shown in FIGS. 1A and 1B.

The software is comprised of the following major modules:

Main menu—provides start up routines and initialization routines for the EFA-2. Upon startup a main menu window is displayed and user commands are available. To enforce correct sequencing of the procedure some commands are not available until prerequisite steps have been performed.

Patient input and selection—provides services to add/edit a new patient, select previous patients for retest and select a patient for demonstration. Provides interactive forms for the collection of patient data. Protocol information forms are available. After all data is validated, control is return to a Select Patient module, which then returns control to the Main menu.

Protocol selection—provides for selection of the protocol (sequence of steps) for the current test. The software has available several pre-defined protocols and custom protocols can be added as needed. Each protocol gives the operator instructions as to what the patient should do and instructions on the placement of the sensor(s). This module also provides support for muscle group, range of motion, nerve conduction velocity study, temperatures, cardiac placement, including facial, cervical, thoracic, upper/lower extremities, lumbosacral, chest, cardiac, nerve selections and temperature.

Sensor(s) verification—provides testing of the sensor(s) to view accuracy of placement, data and activity.

Data acquisition—provides data capture routines. Data is collected and monitored via the EFA-2. If a lead fail is detected during the data capture, the acquisition module cancels the data capture and sends a warning to the operator. A successful data capture results in a data file being saved to an internal hard drive. If the test is being performed in real time the results are displayed immediately.

Treatment delivery—provides for delivery of site-specific treatment modalities.

Data transfer—provides routines to transfer the data to a central site for processing. The transfer can be over an Internet connection (either dial-up or networked) or by electronic media through a delivery service (USPS, UPS etc.).

Remote monitoring—allows testing to be conducted from a remote location.

Operation:

To conduct a test, the subject's (person or animal) muscle activity, cardiac activity, range-of-motion, functional activity, nerve conduction velocity, brain activity and temperature are analyzed. The analysis is performed by attaching sensor(s) from the EFA-2 to selected muscle groups, nerve groups and or cardiac groups on the subject and measuring their electrical activity. The measurement process for the muscle groups are as follows:

a) measure facial muscle groups by placing a range-of-motion sensor(s) on the subject's head and an EMG sensor(s) on the facial muscles and taking measurements while the subject,
   1) at rest,
   2) perform the range-of-motion and functional evaluation protocols, and
   3) return to rest, b) measure cervical muscle groups on a subject by placing a range-of-motion on the subject's head and taking measurements while the subject is:
   1) at rest,
   2) perform the range-of-motion and functional evaluation protocols, and
   3) return to rest, c) measure the thoracic muscle group by placing the ROM at the center of the subject's torso and shoulders and taking measurements while the subject is:
   1) at rest,
   2) perform the range-of-motion and functional evaluation protocols, and
   3) return to rest, d) measure the chest muscle groups by placing the ROM and EMG sensors on the required muscles and the ROM on the subject's torso and shoulders and taking measurements while the subject is:
   1) at rest,
   2) perform the range-of-motion and functional evaluation protocols, and
   3) return to rest, e) measure the lumbosacral muscle group by placing the required EMG sensor(s) and ROM at the center of the subject's lower spine and taking measurements while the subject is:
1) at rest,
2) perform the range-of-motion and functional evaluation protocols, and
3) return to rest, f) measure the lower and upper extremities on a subject by placing bilateral EMG sensor(s) on the front and back of the upper and lower extremities and also placing a ROM on the extremities and taking measurements while the subject is:
1) at rest,
2) perform the range-of-motion and functional evaluation protocols and assessments, and
3) return to rest, g) measure the foot muscles of a subject by placing the required EMG sensor(s) on and the ROM in the correct place, and taking measurement while the subject is:
1) at rest,
2) perform the range-of-motion and functional evaluation protocols, and
3) return to rest, h) for the upper extremities in humans, muscle groups are monitored with the EMG and ROM in addition to the subject resting and performing range of motion tests the subject is also tested for grip, pinch and then return to rest. The muscle readings are also true for the digits in the upper and lower extremities. The digits in the upper extremities also include temperature, pinch and grip, and the lower extremities test range of motion. In addition, cardiac output is monitored with EMG range of motion while the subject is:
1) at rest,
2) performing range-of-motion and functional evaluation protocols, and
3) return to rest.

Nerve conduction velocities can also be monitored while the subject is controlled for temperatures with pre-set sensor(s) and range of motion measurements.

Blood flow and heart rate can also be monitored.

Brain activity can also be monitored.

Treatment can also be delivered to any muscle or nerve with the site-specific capabilities of electrical stimulation and ultrasound.

The testing can also be conducted from a remote location.

The system is integrated into one complete package.

The Muscle Groups are Classified as Follows:

a) the facial muscles are comprised of all of the muscles in the face,
b) the cervical muscles in humans, with the following same analogy for animals are comprised of all the muscles is the anterior and posterior cervical musculature and lateral musculature, including, but not limited to: sternocleidomastoid, scalene paracervical and upper trapezii,
c) the thoracic muscle groups in humans, with the same analog in animals, are comprised of, but not limited to: mid trapezii, lower trapezii, paraspinal muscles T5-T8, T8-T12, terres, serratus and lotisimus dorsi,
d) the chest musculature is comprised of, but not limited to: the pectoralis muscles, the abdominal muscles and the same analogy in animals,
e) the lumbosacral muscle group is comprised of, but not limited to, paraspinal muscles L1-S1 quadratus lumborum, gluteal musculature, abdominal and hamstrings, with the same corresponding musculature in animals,
f) the lower extremity muscle groups are comprised of but not limited to: all muscles in the pelvis, legs and feet, and with the same analogy in animals,
g) the foot muscle groups is comprised of but is not limited to muscles in the feet, with the same analogy in animals,
h) the upper extremity groups are comprised of but are not limited to: deltoid, biceps, triceps, wrist flexors and extensors and thenar muscles, and
i) the hand muscle group is comprised of all muscles in the hand.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

The invention claimed is:

1. An electro diagnostic functional assessment unit (EFA-2) comprising:
at least one EMG sensor,
at least one EMG/EKG sensor having means for sensing cardiac response of a person's muscle groups, wherein the outputs from said at least one EMG/EKG sensor(s) are applied to and processed by said EFA-2,
at least one EMG sensor having means for producing a current for sensing the amplitude, frequency and conduction velocity of specific nerves of a person's muscle groups or nerve fibers, wherein the output from said at least one EMG sensor is applied to and processed by said EFA-2,
at least one nerve conduction velocity (NCV) sensor having means for monitoring the nerve conduction velocity of a person, wherein the output from said at least one NCV sensor is applied to and processed by said EFA-2,
at least one range of motion (ROM) device that generates data through the use of potentiometers, goniometers, accelerometers, video or electro magnetic sensors, wherein said ROM device is configured to measure a person's range of motion, lateral movement, flexion, extension, rotation, abduction, joint capabilities, speed and consistency in either upper or lower extremities or spine, wherein the output from said ROM device is applied to and processed by said EFA-2,
at least one functional capacity evaluation (FCE) sensor having means for measuring a person's lift, push or pull capability, wherein the output of said at least one FCE sensor(s) is applied to and processed by said EFA-2,
at least one grip sensor having means for measuring a person's grips strength, wherein the output of said at least one grip sensor is applied to and processed by said EFA-2,
at least one pinch sensor having means for measuring a person's pinch strength, wherein the output of said at least one pinch sensor is applied to and processed by said EFA-2, and
at least one treatment delivery mechanism having means for delivering site-specific treatment, wherein the output from said at least one treatment delivery mechanism is applied to and processed by said EFA-2 which is configured to perform site-specific treatment.

* * * * *